United States Patent [19]

Fazio et al.

[11] Patent Number: 5,006,567

[45] Date of Patent: Apr. 9, 1991

[54] PROCESS FOR FOAMING POLYMER COMPOSITIONS WITH HYDRAZONE COMPOUNDS AND COMPOSITIONS ASSOCIATED THEREWITH

[75] Inventors: Michael J. Fazio; Richard A. Wolf; Edwin J. Wilson, all of Midland, Mich.; Susan Wollowitz, Walnut Creek, Calif.

[73] Assignee: The Dow Chemical Company, Midland, Mich.

[21] Appl. No.: 255,572

[22] Filed: Oct. 11, 1988

[51] Int. Cl.$^5$ ................................................. C08J 9/10
[52] U.S. Cl. ..................................... 521/95; 521/180; 521/139; 521/146; 521/147; 521/148
[58] Field of Search ................. 521/95, 139, 146, 147, 521/148, 180

[56] References Cited

U.S. PATENT DOCUMENTS

| | | |
|---|---|---|
| 3,269,962 | 8/1966 | Eichhorn . |
| 3,277,028 | 10/1966 | Parker et al. . |
| 3,993,609 | 11/1976 | Kamens et al. . |
| 4,029,615 | 6/1977 | Kamens et al. . |
| 4,322,502 | 3/1982 | Stott et al. . |
| 4,722,640 | 9/1988 | Wolf et al. . |
| 4,743,623 | 5/1988 | Wolf et al. . |

FOREIGN PATENT DOCUMENTS

| | | |
|---|---|---|
| 1309032 | 4/1966 | France . |
| 67550 | 9/1968 | Japan . |
| 55-055716 | 11/1981 | Japan . |
| 790312 | 2/1958 | United Kingdom . |
| 1052634 | 1/1962 | United Kingdom . |

OTHER PUBLICATIONS

O'Connor, "Tautomerism in Phenylhydrazones," 26 J. Org. Chem. 4375, (1961).

Bellamy et al., "Studies on the Possible Interconversion of Phenylhydrazones and Phenylazoalkanes. Part 1," 1965, J. Chem. Soc. 2788, (1965).

Wolf et al., "Process for Foaming Polymeric Compositions with Organic Azo Compounds and Compositions Associated Therewith," Ser. No. 221,696, (filed Jul. 20, 1988).

*Primary Examiner*—Morton Foelak

[57] ABSTRACT

Hydrazone compounds having two organic moieties joined by a hydrazone group, such as phenylacetone t-butyl hydrazone, are useful blowing agents for foaming polymers, such as bisphenol A/phosgene polycarbonate at temperatures above about 280° C., and particularly at about 300° C. to about 310° C. Polycarbonate polymers formed using the hydrazones as foaming agents show a high impact strength.

15 Claims, No Drawings

PROCESS FOR FOAMING POLYMER COMPOSITIONS WITH HYDRAZONE COMPOUNDS AND COMPOSITIONS ASSOCIATED THEREWITH

BACKGROUND OF THE INVENTION

This invention relates to processes for foaming polymer compositions, compositions useful for preparing foamed polymer compositions and solid foamed polymer compositions.

Foamed polymer compositions are cellular structures which typically comprise a gas dispersed throughout a solid. Such foamed compositions can exhibit a lower density and weight, but a substantially equivalent strength to non-foamed compositions. An example of a commercial foamed thermoplastic polymer composition is a polycarbonate polymer foamed with 5-phenyl tetrazole compound.

Polycarbonate polymers are derived from reactions of dihydroxy organic compounds. Commonly used polycarbonates are derived from dihydric phenols and carbonic acids or derivatives such as phosgene. Such thermoplastic polymers are suitable for the manufacture of molded parts wherein impact strength, rigidity, toughness, heat resistance and excellent electrical properties are desired.

Thermoplastic polymer compositions are foamed by dispersing a blowing or foaming agent throughout the polymer composition at a temperature at which the polymer composition is thermoplastic and the foaming agent is stable. The polymer composition and foaming agent are then subjected to conditions under which the foaming agent decomposes into gaseous products which can cause the volume of the polymer composition to increase. Unfortunately, many foaming agents, including 5-phenyl tetrazole, decompose into products which adversely affect the polymer composition. For example, the decomposition products of 5-phenyl tetrazole undesirably react with polycarbonate polymers, lowering the molecular weight, and causing brittleness in the final polycarbonate foam.

In view of the disadvantages of known methods, it would be desirable to foam polymer compositions using foaming agents whose degradation products do not adversely affect the polymer compositions in which they are used.

SUMMARY OF THE INVENTION

One aspect of the present invention is a process for foaming a thermoplastic polymer comprising the steps of:

(a) dispersing throughout the molten thermoplastic polymer a foaming amount of foaming agent which contains a hydrazone compound having:
  (1) a hydrazone group having a first hydrazone nitrogen atom and a second hydrazone nitrogen atom joined by a single bond,
  (2) a first organic moiety having a single bond from a carbon atom in the first organic moiety to the first hydrazone nitrogen atom,
  (3) a hydrogen atom bonded to the first hydrazone nitrogen atom, and
  (4) a second organic moiety having a double bond from a carbon atom in the second organic moiety to the second hydrazone nitrogen atom, said first and second organic moieties being chosen such that said hydrazone compound is substantially stable with respect to thermal decomposition at temperatures up to at least 200° C. and such that said hydrazone compound substantially decomposes to liberate gas at a temperature at which the polymer does not experience substantial thermal degradation; and (b) subjecting the foaming agent to temperature conditions under which said hydrazone compound substantially decomposes and foams the polymer.

Another aspect of the present invention is a composition useful for making foamed thermoplastic polymers comprising:

(a) a polycarbonate or carbonate-containing copolymer or a blend comprising such a polycarbonate or copolymer; and (b) at least a foaming amount of a hydrazone compound having:
  (1) a hydrazone group having a first hydrazone nitrogen atom and a second hydrazone nitrogen atom bonded by a single bond,
  (2) a first organic moiety having a single bond from a carbon atom in the first organic moiety to the first hydrazone nitrogen atom,
  (3) a hydrogen atom bonded by a single bond to the first hydrazone nitrogen atom, and
  (4) a second organic moiety having a double bond from a carbon atom in the second organic moiety to the second hydrazone nitrogen atom, said first and second organic moieties being chosen such that said hydrazone compound is substantially stable with respect to thermal decomposition at temperatures up to at least 200° C. and such that said hydrazone compound substantially decomposes liberating gas at a temperature below the decomposition temperature of the polycarbonate, copolymer or blend.

A third aspect of the present invention is a foamed polymer composition which has been foamed by the process of the present invention.

Unfoamed compositions of the present invention can be used in the process of the present invention to make foamed polymer compositions of the present invention. The foamed polymer compositions of the present invention have unusually high impact strength as compared with polymers foamed using known agents such as 5-phenyl tetrazole. The composition, process and product of the present invention can be used in connection with a plastic molding process to produce strong molded plastic parts.

DETAILED DESCRIPTION OF THE INVENTION
Hydrazones Used in the Present Invention:

Foaming agents used in the present invention comprise hydrazone compounds. Although the foaming agent may further comprise other compounds known to be useful in foaming agents, hydrazone compounds of the present invention are preferably the major foaming ingredient and more preferably the only foaming ingredient.

Hydrazone compounds used in the present invention preferably comply with one of the following formulae:

$$R^2(=N-NHR^1)_a \qquad (1)$$

or

$$R^1-(NH-N=R^2)_b \qquad (2)$$

wherein $R^1$ corresponds to the first organic moiety of the hydrazone compound and $R^2$ corresponds to the second organic moiety. $R^1$ and $R^2$ have carbon atoms at the site bonded to the hydrazone nitrogen and are chosen such that the hydrazone group is substantially stable with respect to thermal decomposition at temperatures of at least 200° C. Subscripts a and b represent a number of hydrazone groups and organic moieties equal to 1 or more.

As the above formulae show, hydrazone compounds used in the present invention may have one or more hydrazone groups. Preferably, hydrazone compounds used in the present invention comprise no more than about 3 hydrazone groups, so that a or b is no more than about 3. More preferably, hydrazone compounds used in the present invention comprise no more than about 2 hydrazone groups, so that a or b is no more than 2. Hydrazone compounds with multiple hydrazone groups preferably contain only one second organic moiety, and comply with Formula (1).

When the hydrazone compound contains only one hydrazone group, a and b are 1 and it complies with formula (3) set out below:

$$R^1-NH-N=R^2 \qquad (3)$$

wherein $R^1$ and $R^2$ have the definitions previously given.

The first and second organic moieties preferably comprise at least 2 carbon atoms each and more preferably at least 3 carbon atoms each. Practical considerations such as solubility and steric hindrance limit the maximum size of the first and second organic moieties. Each of the first and second organic moieties preferably comprises no more than about 12 carbon atoms; more preferably, no more than about 10 carbon atoms. The first organic moiety most preferably comprises no more than about 6 carbon atoms.

The first organic moiety ($R^1$) may be aromatic, aliphatic or aliphatic-aromatic. Aliphatic moieties may be either straight-chain or cyclic and either saturated or unsaturated. The carbon atom which is bonded to the hydrazone nitrogen is preferably either a saturated carbon or part of an aromatic ring system. More preferably, all aliphatic carbon atoms in the first organic moiety are saturated. The first organic moiety may be, for example, alkyl, cycloalkyl, aryl or alkaryl. More preferred examples include phenyl, benzyl, tolyl, cyclopentyl, cyclohexyl, butyl, pentyl, hexyl, heptyl or octyl groups and isomers or analogs thereof.

The second organic moiety ($R^2$) comprises an aliphatic moiety double bonded to the hydrazone group. The aliphatic moiety may be cyclic, branched or linear. It is preferably saturated. The aliphatic moiety may have aromatic substituents. The second organic moiety may be, for example, alkyl, cycloalkyl or alkaryl. More preferred examples are derived from benzaldehyde, acetone, butanone, pentanone, hexanone, phenylbutanone, cyclohexanone, pentanedione or hexanedione and isomers or analogs thereof.

Both the first and second organic moieties may contain heteroatoms, such as nitrogen, oxygen, sulfur or halogens, at points where the heteroatom is not bonded directly to a hydrazone nitrogen. For instance, the first organic moiety may be a pyridinyl moiety or a haloalkyl or haloaromatic moiety, and the second organic moiety may be a halogenated alkyl or alkaryl group. The first and second organic moieties preferably consist of carbon, hydrogen and halogens. The first and second organic moieties are more preferably hydrocarbyl (consisting of carbon and hydrogen atoms).

Examples of hydrazone compounds which may be used as foaming agents include benzaldehyde phenylhydrazone, benzaldehyde t-butylhydrazone, acetone phenylhydrazone, 3,3-dimethyl-2-butanone phenylhydrazone, 4-phenyl-2-butanone t-butylhydrazone, 2,5-hexanedione bis-(t-butylhydrazone), cyclohexanone t-butylhydrazone and 3,5,5-trimethylcyclohex-2-ene-one t-butylhydrazone and isomers and analogs thereof.

Hydrazone compounds used in the present invention are substantially stable with respect to thermal decomposition at about 200° C.; preferably, at about 230° C.; and more preferably, at about 250° C. For purposes of this discussion, a hydrazone compound which is substantially stable has a half-life under process conditions of at least about 6 hours, preferably at least about 12 hours and more preferably at least about 24 hours.

Hydrazone compounds used in the present invention preferably undergo substantial thermal decomposition of the hydrazone group at about 350° C.; more preferably, at about 325° C.; more highly preferably, at about 310° C.; and most preferably, at about 300° C. For the purposes of this discussion, a hydrazone compound undergoes substantial thermal decomposition if its half-life under process conditions is no more than about 10 minutes, preferably no more than about 3 minutes; more preferably no more than about 1 minute; and most preferably no more than about 30 seconds. The most preferred hydrazone compounds thermally decompose at a rate desirable for blowing agents at between about 280° C. and about 310° C.

Hydrazone compounds of the present invention are prepared from hydrazine derivatives of the first organic moiety ($R^1$). Some hydrazine compounds, such as t-butyl hydrazine hydrochloride, phenyl hydrazine hydrochloride and tolyl hydrazine hydrochloride, are commercially available. Others can be prepared from a primary amine of the first organic moiety ($R^1$). Amines useful for synthesizing hydrazines preferably conform to the formula:

$$R^1-NH_2$$

wherein $R^1$ complies with the limits and preferred embodiments set forth previously. Common amines which may be used include aniline, t-butyl amine, isopropyl amine, n-propyl amine, cyclohexyl amine, toluidine, benzyl amine and homologs of those compounds.

The amine can be converted to the hydrazine by known processes such as are described in 12 Kirk-Othmer Encyclopedia of Chemical Technology, *Hydrazine and Its Derivatives*, 734, 743–46 (1980), which is incorporated herein by reference. For instance, alkyl hydrazines can be synthesized by the reaction of chloramine with a monoalkylamine.

Some aromatic hydrazines can be synthesized by a similar method, but a broader range of compounds are synthesized by a two-step procedure described in Arcus and Schaffer, *m-Hydrazinostyrene*, 1958 *J. Chem. Soc.* 2428 (1958) which is incorporated herein by reference. First, the aromatic amine is converted to an aromatic diazonium ion, such as converting aniline to a phenyldiazonium ion, by reaction with cold aqueous sodium nitrite, for instance at about 0° C. Second, the diazonium ion is converted to the corresponding hydrazine hydrochloride by reaction with stannous chloride in the presence of hydrochloric acid. The hydrazine hydrochloride may be stored for months under dry conditions at about 10° C. At the time for use, the basic hydrazine is generated by extraction from 2N sodium hydroxide with methylene chloride, or similar techniques.

The hydrazone is formed by addition of an acyl compound to the hydrazine as described in Ardagh et al., "An Investigation of Some Properties of Phenylhydrazine and Factors Affecting Hydrazone Formation", 47 *J. Am. Chem. Soc.* 2976 (1925), which is incorporated herein by reference. The hydrazine is contacted with a ketone or aldehyde at cool temperatures, such as about 10° C., in a solvent, such as methanol. The aliphatic group of the ketone or aldehyde forms the aliphatic group of the second organic moiety of the hydrazone ($R^2$). Common aldehydes and ketones which may be used include acetone, butanone, cyclohexanone, hexanedione, phenylbutanone, benzophenone, benzaldehyde, acetaldehyde, propionaldehyde and isomers and homologs thereof.

Acyl compounds useful in the present invention are frequently well-known and commercially available. Other ketones can be formed by well-known reactions such as Friedel-Crafts acylation of aromatic compounds or oxidation of alcohols with chromium trioxide, chromate salts or dichromate salts. Such reactions are described in G. M. Loudon, *Organic Chemistry* 592–93, 736–37 (Addison-Wesley Publishing Co. 1984), which is incorporated herein by reference.

The Process of the Present Invention:

Techniques to foam and shape a polymer using a thermally activated foaming agent are well-known in the art of polymer chemistry. The process of the present invention employs similar procedures using the foaming agents described previously.

The polymer composition to be foamed is preferably one which has a glass transition temperature below the decomposition temperature of the hydrazone compound and is substantially stable with respect to thermal degradation at temperatures at which the hydrazone compound undergoes substantial thermal decomposition. The polymer preferably has a glass transition temperature at or below about 250° C. The polymer is more preferably stable up to about 315° C. and more highly preferably, up to about 325° C. Examples of suitable thermoplastic polymers include styrene copolymers such as styrene-acrylonitrile (SAN) or acrylonitrile-butadiene-styrene (ABS) copolymers; polyphenylene oxide blends; and polycarbonates or polycarbonate blends. The polymer to be foamed is preferably a polycarbonate, a thermoplastic carbonate-containing copolymer, or a thermoplastic blend comprising polycarbonate or carbonate-containing copolymer. The polymer is more preferably polycarbonate.

In the first step of the process, a foaming agent as described previously is dispersed throughout the molten polymer. That step may be accomplished, for instance, by first heating the polymer to a molten state and second mixing in the blowing agent; or by first mixing the foaming agent with solid polymer pellets and second heating the polymer to a molten state; or by mixing the foaming agent throughout a molten polymer, cooling the polymer to form a solid foaming agent/polymer concentrate, and later remelting the concentrate in a mixture with polymer containing no foaming agent.

The foaming agent is preferably dispersed evenly throughout the polymer composition by stirring or agitation to give a substantially uniform foaming effect during subsequent foaming. When the polymer is polycarbonate or a polycarbonate blend, the hydrazone compounds are frequently highly soluble in the molten polymer. With other polymers, it may be advantageous to add a compatibilizing or stabilizing agent to maintain the foaming agent in a dissolved or suspended state.

The optimum concentration of the foaming agent in the polymer varies in a manner familiar to those skilled in the art, depending upon factors such as the foaming agent used, the polymer being foamed, the conditions under which foaming is carried out and the extent of foaming desired. The ratio of foaming agent to polymer is ordinarily only a small percentage by weight. It is preferably no less than about 0.01 percent by weight, more preferably no less than about 0.15 percent by weight; and preferably no more than about 5 percent by weight, more preferably no more than about 0.30 percent by weight.

During the dispersion step the polymer is heated to a temperature at which the polymer is fluid but the hydrazone does not undergo substantial thermal decomposition. The minimum temperature necessary depends upon the polymer, but is ordinarily at least about 200° C. to about 240° C. The maximum temperature of the dispersion step depends upon the hydrazone being used, but is preferably about 280° C. and more preferably about 250° C.

Other additives, such as coloring agents, plasticizers, antioxidants, stabilizers and desiccants, are known in the art to be useful in polymers. Additives which are inert with respect to the hydrazone compound and are not contraindicated by the particular polymer and process employed may optionally be added to the molten polymer composition containing the dispersed blowing agent. Additives preferably make up no more than about 50 percent of the composition by weight.

After the foaming agent is dispersed throughout the polymer, the polymer composition is subjected to temperature conditions which cause the hydrazone compound to decompose liberating nitrogen gas and organic decomposition products. Other conditions, such as intense light, high sheer rate or exposure to ultrasound vibrations may accelerate the decomposition of some hydrazone compounds at lower temperatures. Preferably, only heat is used to decompose the hydrazone compound.

The foaming step is carried out at a temperature high enough that the polymer is molten and the hydrazone compound undergoes substantial thermal decomposition. The temperature is preferably above about 250° C., more preferably at least about 280° C. and most preferably at least about 300° C.

The maximum temperature of the foaming step should be low enough that the polymer does not undergo substantial thermal degradation. For instance, many polycarbonates degrade rapidly at temperatures above about 325° C. and should not be foamed at beyond that temperature. Even at temperatures below those which cause rapid thermal degradation of the polymer, the polymer may experience some slow thermal degradation. Therefore, the temperature of the foaming step is preferably as low as is feasible, and the foaming step is preferably not prolonged unduly. Preferred maximum temperatures for the foaming step are the preferred temperatures at which the hydrazone compound decomposes as previously described.

It is consistent with the description of this process to attain temperatures for dispersion and foaming by continuously heating the polymer from about ambient temperature through its melting temperature, at which dispersion takes place, up to the desired foaming temperature.

Decomposition of the foaming agent is preferably carried out either in a forming apparatus or under pressure such that the released gases cannot expand substantially. If the hydrazone compound is decomposed under pressure, the composition is subsequently injected into a forming apparatus under conditions which allow the gas bubbles formed by the foaming agent to expand. Once the composition is in the forming apparatus it is permitted to harden by cooling. The forming apparatus may be any mold or device which can shape the foamed polymer into a shape suitable for its intended use or the next step in its processing. Such devices are well-known in the art, as is their use.

An example of the preferred use of this process, not intended to limit either the specification or the claims, is in the injection molding of a thermoplastic polycarbonate or polycarbonate blend. The polymer is beyond its glass transition temperature, preferably to about 250° C. The foaming agent is dispersed throughout the molten polymer. The composition is subjected to a temperature sufficient to decompose the hydrazone compound, preferably about 300° C. to about 310° C., under pressures such that the gases liberated by the decomposition cannot substantially expand. Thereafter, the polymer composition is maintained under pressure until it is injected into a mold which is suitable to form it into its desired shape. When the polymer composition experiences reduced pressure in the mold, the liberated gas forms bubbles in the polymer, thereby foaming the polymer. The foamed polymer is permitted to cool in the mold until it is substantially hardened. Preferably, the cooling process takes no more than about one or two minutes.

Compositions Useful in the Practice of the Invention

Compositions useful to practice the process described above comprise a foaming agent as previously described and a polycarbonate, a thermoplastic carbonate-containing copolymer or a thermoplastic polymer blend comprising polycarbonate or carbonate-containing copolymer. Polymers, copolymers or blends preferably comply with the criteria set out previously in describing polymers suitable for the previously described process. The polymer is most preferably polycarbonate.

Polycarbonate polymers can be prepared by conventional methods. Suitable methods and compositions are disclosed, for example, in U.S. Pat. Nos. 4,066,611; 4,221,645; 4,330,662; 4,504,634 and 4,544,706. Further, the carbonate polymers useful in this invention can be aromatic carbonate polymers as described in U.S. Pat. Nos. 3,036,036; 3,036,037; 3,036,038 and 3,036,039; and polycarbonates of bis(aryl-hydroxyphenyl) alkylidenes (i.e., the bisphenol A type diols) including their aromatically and aliphatically substituted derivatives, such as those disclosed in U.S. Pat. Nos. 2,999,835; 3,038,365 and 3,334,154; and carbonate polymers derived from other aromatic diols such as described in U.S. Pat. No. 3,169,121. Polyester carbonate polymers are also suitably employed in this invention. Such polymers can be derived from at least two different dihydric phenols or a dihydric phenol and a glycol or a hydroxy- or acid-terminated polyester or a dibasic acid. Such mixtures can provide carbonate copolymer or interpolymer compositions. Suitable methods and combinations of such ester carbonate copolymers are described in U.S. Pat. Nos. 3,169,121; 4,287,787; 4,156,069; 4,260,731; 4,330,662; 4,360,656; 4,374,973; 4,225,556; 4,388,455; 4,355,150 and 4,105,633. All patents identified in this paragraph are incorporated herein by reference.

The foaming agents used in the composition have the same limits and preferred embodiments described previously and comprise the hydrazone compounds which are described hereinbefore.

Compositions of the present invention may be prepared for immediate use in foaming the polymer, or may be prepared as a concentrate of foaming agent in polymer. A relatively small amount of the concentrate may be added later to, and dispersed throughout, a larger amount of molten polymer which has no foaming agent, and the entire composition may be subjected to conditions which decompose the foaming agent. Concentrate compositions are a convenient way to package, transport, market and use such a foaming agent in the process of this invention.

If the composition is made for immediate use, the proportions of foaming agent to polymer preferably comply with those parameters set out previously in describing the process of this invention. If the composition is intended to be a concentrate, the foaming agent preferably makes up 2 to 10 percent by weight of the composition. More preferably, the foaming agent is about 5 percent of the composition by weight.

Compositions may be made simply by heating the thermoplastic polymer to a temperature at which it is molten but the foaming agent is substantially stable. The foaming agent is then added to the polymer and dispersed throughout the polymer by known methods such as mixing with stirring or agitation, until that dispersion is substantially even throughout the entire composition. Other desired additives or components which are inert with respect to the foaming agent under process conditions may also be added. The composition should then be used or cooled to solidifying temperatures within a short time to minimize incidental decomposition of the foaming agent. Concentrate compositions may be pelletized or otherwise formed to a particulate physical structure which can easily be measured, packaged and transported.

Foamed Polymer Compositions of the Invention

A third aspect of the instant invention is a foamed polymer composition prepared by the process described previously. Polymers, foaming agents and the process conditions needed to make those blown compositions are described above. Preferred reagent and process parameters are those set out above. Polymers are preferably polycarbonates or polycarbonate blends, such as those identified in describing the unfoamed compositions of the present invention.

The foamed polymer composition of this invention can have a density 1 to 50 percent lower than an unfoamed polymer composition. Foamed polycarbonate compositions of this invention exhibit impact resistance superior to polycarbonates foamed using 5-phenyl tetrazole.

ILLUSTRATIVE EXAMPLES

The following examples are for illustrative purposes only and are not to be taken as limiting the scope of either the specification or the claims. Unless stated otherwise, all parts and percentages are by weight.

Preparation of Hydrazones (Not an Example of the Invention)

(a) Phenylacetone t-butyl hydrazone

A solution of 50.46 g t-butyl hydrazine hydrochloride and 32 g of 50 percent aqueous sodium hydroxide in 70 ml of water is stirred in an ice water bath. About 50.22 g of phenylacetone is added with stirring. The mixture is stirred and allowed to warm to ambient temperature over about 12 hours. Pentane (300 ml) is added to the solution with agitation, and then separated. The pentane layer is washed twice with water, dried over anhydrous sodium sulfate, and filtered. The pentane is removed under vacuum. The title compound is isolated as a fraction distilled under 0.9 mm pressure at 89° C.-103° C. About 56.5 g of the title compound are recovered for a 74 percent yield, based upon the phenylacetone added.

(b) 4-Phenyl-2-butanone t-butyl hydrazone

A solution of 50.46 g t-butyl hydrazine hydrochloride and 32 g of 50 percent aqueous sodium hydroxide in 70 ml of water is stirred in an ice water bath. About 55 g of 4-phenyl-2-butanone is added with stirring. The reaction and isolation are continued as in Example (a). The title compound is isolated as a fraction distilled under 0.9 mm pressure at 110° C.-119° C. The yield is about 49 percent based upon the initial amount of 4-phenyl-2-butanone added.

(c) 2,5-Hexane-di-one bis-(t-butylhydrazone)

The procedure of Example (a) is followed using about 67.6 g (0.54 mole) of t-butyl hydrazine hydrochloride and about 28.5 g (0.25 mole) of 2,5-hexane-di-one. The title compound is isolated as a fraction distilled at about 106° C.-114° C. under 1.0 mm Hg pressure. The yield is about 60 percent based upon the initial amount of hexane-di-one.

(d) Acetophenone phenylhydrazone

Phenylhydrazine (10.8 g, 0.10 mole) is added to 20 g (0.10 mole) of acetophenone with stirring at about 15° C. The reaction produces a slight exotherm and the solution solidifies. The title product is allowed to sit for about 12 hours at room temperature and is then used without further purification.

(e) Benzaldehyde phenylhydrazone

The procedure of Example (d) is followed using about 18.6 g (0.10 mole) of benzaldehyde in place of the acetophenone.

EXAMPLE 1

Foaming Process Utilizing Hydrazones

Pellets of a bisphenol A/phosgene polycarbonate structural resin, commercially available as CALIBRE® 7070 (registered trademark of The Dow Chemical Company), are dried in an air recirculating oven for 4 hours at 250° F. according to recommended drying procedures for the product. They are removed from the oven and allowed to cool to about 150° F. Phenylacetone t-butylhydrazone (0.3 weight percent) is added and the mixture is tumble blended until the liquid hydrazone is dispersed evenly on the resin pellets. The pellets are placed in the feed hopper of a CINCINNATI MILACRON® 200-ton injection molding machine equipped with an 8½-inch by 11-inch by ¼-inch cavity plaque mold. The barrel temperature of the injection molding machine is controlled to produce a melt temperature at the nozzle end of approximately 585° F. (307° C.). The cycle time of the molding machine is controlled at 2 minutes so that the polycarbonate and hydrazone reside in the heated barrel for approximately 6 minutes.

Molded plaques are prepared and cut to produce test specimens in strips ½ inch wide by 5 inches long. The density of the strips is measured at approximately 0.98 g/cm$^3$. The impact strength of these strips is measured using a 10-lb pendulum to strike the ½ inch wide side in an unnotched Izod test configuration. The strip has an impact strength of 10±0.09 ft-lb/in.

EXAMPLE 2

The process of Example 1 is repeated utilizing 0.3 percent phenyl butanone t-butyl hydrazone, 0.3 percent benzaldehyde phenyl hydrazone and 0.15 percent hexanedione bis-(t-butylhydrazone). The results are shown hereinafter in Table I.

TABLE I

|  |  | Melt Temp (°C.) | Density (g/cc) | Impact Strength (ft-lb/inch) |
|---|---|---|---|---|
| 0.3% | phenylbutanone t-butyl hydrazone | 302 | 0.99 | 10.7 ± 0.9 |
|  |  | 307 | 0.98 | 10.0 ± 0.9 |
|  |  | 315 | 0.97 | 9.0 ± 0.7 |
|  |  | 329 | 0.98 | 7.3 ± 0.5 |
| 0.3% | benzaldehyde phenyl hydrazone | 315 | 0.98 | 8.7 ± 1.1 |
|  |  | 329 | 0.99 | 8.6 ± 0.5 |
| 0.15% | hexanedione bis(t-butyl hydrazone) | 310 | 1.01 | 13.0 ± 2.7 |
|  |  | 329 | 0.97 | 10.1 ± 1.4 |
| 0.25% | 5-phenyl tetrazole+ | 302 | 0.95 | 6.2 ± 0.5 |
|  |  | 321 | 0.95 | 6.3 ± 1.2 |
|  |  | 329 | 0.92 | 5.3 ± 0.5 |

+- Not an example of the invention

What is claimed is:

1. A process for foaming a thermoplastic polymer comprising the steps of:
   (a) dispersing throughout the molten thermoplastic polymer a foaming amount of foaming agent which contains a hydrazone compound having:
      (1) a hydrazone group having a first hydrazone nitrogen atom and a second hydrazone nitrogen atom joined by a single bond,
      (2) a first organic moiety having a single bond from a carbon atom in the first organic moiety to the first hydrazone nitrogen atom,
      (3) a hydrogen atom bonded to the first hydrazone nitrogen atom, and
      (4) a second organic moiety having a double bond from a carbon atom in the second organic moiety to the second hydrazone nitrogen atom,
   said first and second organic moieties being chosen such that said hydrazone compound is substantially stable with respect to thermal decomposition at temperatures up to at least 200° C. and such that said hydrazone compound substantially decomposes to liberate gas at a temperature at which the polymer does not undergo substantial thermal degradation; and
   (b) subjecting the foaming agent to temperature conditions in excess of 200° C. under which said hydrazone compound substantially decomposes and foams the polymer.

2. A process of claim 1 wherein the hydrazone complies with one of the following formulae:

$$R^2(=N-NHR^1)_a \qquad (1)$$

or $$R^1-(NH-N=R^2)_b \quad (2)$$

wherein $R^1$ is a first organic moiety containing between 2 and 12 carbon atoms; $R^2$ is a second organic moiety containing between 2 and 12 carbon atoms; and a and b represent a number of hydrazone groups and organic moieties equal to 1 or more.

3. A process of claim 1 wherein the hydrazone compound contains no more than about 3 hydrazone groups and wherein the first and second organic moieties each contain between 2 and 12 carbon atoms.

4. A process of claim 3 wherein the hydrazone compound contains only one second organic moiety, and wherein first and second organic moieties of the hydrazone compound are hydrocarbyl moieties.

5. A process of claim 4 wherein the foaming step is carried out at a temperature of at least about 280° C.

6. A process of claim 5 wherein the polymer foamed is a polycarbonate, a thermoplastic carbonate-containing copolymer, or a thermoplastic blend comprising a polycarbonate or carbonate-containing copolymer and wherein the hydrazone compound contains no more than two hydrazone groups and wherein the first and second organic moieties of the hydrazone compound each comprise no more than about 10 carbon atoms.

7. A process of claim 6 wherein the polymer is heated to a temperature between about 200° C. and about 280° C. during the dispersion step.

8. A process of claim 7 wherein the foaming step is carried out at a temperature between about 300° C. and about 325° C.

9. A process of claim 8 wherein the hydrazone complies with the formula:

$$R^1-NH-N=R^2 \quad (3)$$

wherein $R^1$ is a first organic moiety containing between 3 and 6 carbon atoms and $R^2$ is a second organic moiety containing between 3 and 10 carbon atoms.

10. A process of claim 3 wherein the first organic moiety of the hydrazone compound is a phenyl, benzyl, tolyl, cyclopentyl, cyclohexyl, butyl, pentyl, hexyl, heptyl or octyl group or an isomer or analog thereof.

11. A process of claim 10 wherein the second organic moiety of the hydrazone compound is a derivative of benzaldehyde, acetone, butanone, pentanone, hexanone, phenylbutanone, cyclohexanone, pentanedione or hexanedione or an isomer or homolog thereof.

12. A process of claim 11 wherein the polymer foamed is a polycarbonate, a thermoplastic carbonate-containing copolymer, or a thermoplastic blend comprising polycarbonate or carbonate-containing copolymer.

13. A process of claim 12 wherein the foaming agent is dispersed in the polymer at a temperature between about 200° C. and about 280° C.

14. A process of claim 13 wherein the foaming step is carried out at a temperature between about 280° C. and about 325° C.

15. A process of claim 14 wherein the polymer foamed is a bisphenol A polycarbonate and the hydrazone compound is phenylacetone t-butyl hydrazone, phenyl butanone t-butyl hydrazone, benzaldehyde phenyl hydrazone or hexanedione bis-(t-butylhydrazone).

* * * * *